United States Patent
Burkholz (10) Patent No.: US 8,337,461 B2
(45) Date of Patent: Dec. 25, 2012

(54) SYSTEMS AND METHODS FOR PROVIDING A CONVENTIONAL INTEGRATED CATHETER WITH UNIVERSAL GRIP

(75) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 324 days.

(21) Appl. No.: 12/411,821

(22) Filed: Mar. 26, 2009

(65) Prior Publication Data

US 2010/0249714 A1 Sep. 30, 2010

(51) Int. Cl.
*A61M 5/178* (2006.01)

(52) U.S. Cl. .................... 604/164.01; 604/178; 604/179; 604/180; 604/177; 604/174

(58) Field of Classification Search ............. 604/164.01, 604/174–175, 177–180
See application file for complete search history.

(56) References Cited

U.S. PATENT DOCUMENTS

| | | | |
|---|---|---|---|
| 4,177,809 A | 12/1979 | Moorehead | |
| 5,186,712 A | 2/1993 | Kelso et al. | |
| 5,385,554 A | 1/1995 | Brimhall | |
| 5,676,656 A | 10/1997 | Brimhall | |
| 5,697,914 A | 12/1997 | Brimhall | |
| 5,879,334 A | 3/1999 | Brimhall | |
| 5,913,845 A | 6/1999 | Brimhall | |
| 5,935,110 A | 8/1999 | Brimhall | |
| 6,638,252 B2 | 10/2003 | Moulton et al. | |
| D492,031 S | 6/2004 | Cindrich et al. | |
| 2006/0264833 A1* | 11/2006 | Moulton | 604/164.01 |
| 2006/0270991 A1* | 11/2006 | Adams | 604/164.08 |
| 2007/0270758 A1* | 11/2007 | Hanner et al. | 604/177 |

FOREIGN PATENT DOCUMENTS

| | | |
|---|---|---|
| EP | 1016429 A1 | 5/2000 |
| WO | WO0296494 | 5/2002 |

* cited by examiner

*Primary Examiner* — Bhisma Mehta
*Assistant Examiner* — Edelmira Bosques
(74) *Attorney, Agent, or Firm* — Jeanne Lukasavage; Craig Metcalf; Kirton McConkie (57) ABSTRACT

A universal gripping surface is provided on an intravenous catheter assembly. The universal gripping surface provides a plurality of surfaces whereby a user may grip the catheter assembly in a desired gripping configuration for improved balance and control of the catheter assembly during insertion of the catheter. Additionally, the universal gripping surface includes a guard feature to prevent a user's unintended contact with various components of the catheter assembly whereby the contact may result in an undesirable "over the bevel" condition.

12 Claims, 8 Drawing Sheets

SYSTEMS AND METHODS FOR PROVIDING A CONVENTIONAL INTEGRATED CATHETER WITH UNIVERSAL GRIP

BACKGROUND OF THE INVENTION

The current invention relates to infusion devices, specifically to over-the-needle peripheral intravenous (IV) catheters. Specifically, the invention relates to a peripheral IV catheter assembly with a universal gripping surface. The catheter assembly includes a plurality of gripping surfaces configured to permit multiple gripping configurations common in the medical field. The catheter assembly further includes safety features to prevent premature separation of various components of the assembly. Catheters are widely used throughout the medical community for a wide range of procedures and treatments.

Catheters are commonly used for a variety of infusion therapies. Catheters are used for infusing fluid, such as normal saline solution, various medicaments, and total parenteral nutrition, into a patient, withdrawing blood from a patient, or monitoring various parameters of the patient's vascular system. A common type of intravenous (IV) catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitate insertion of the catheter into the blood vessel. The catheter and the introducer needle are assembled so that the tip of the introducer needle extends beyond the tip of the catheter with the bevel of the needle facing up away from the patient's skin. The catheter and introducer needle are generally inserted at a shallow angle through the patient's skin into a blood vessel.

The process of placing a catheter requires careful balance and control over the catheter. Various configurations and methods for gripping the catheter assembly have been developed to aid the user in maintaining the required balance and control. Among these gripping techniques are "straight grip", "ported grip", and "winged grip" configurations. Preferred gripping configurations vary from one market to another. Preferred gripping configurations are largely determined and established by local trainings, customs, and traditions. Additionally, one gripping configuration may be preferred or taught over another where a market is unable to obtain catheter assembly configured to permit a different gripping configuration.

For example, a straight grip configuration may be taught out of necessity in a market where available catheter assemblies do not include features to permit a ported grip or winged grip configuration. Thus, users in these markets must curtail their technique and skills to accommodate the available catheter assemblies, rather than use a gripping technique that best suits the user's and patient's needs.

Accordingly, there is a need in the art for a catheter assembly incorporating a universal gripping surface that will allow users to select the most appropriate gripping configuration. There is a further need to provide a universal grip incorporating design features to allow a user to securely grip the catheter assembly yet prevent premature separation of the catheter assembly components. Such a universal gripping surface is disclosed herein.

BRIEF SUMMARY OF THE INVENTION

In order to overcome the limitations discussed above, the present invention relates to a plurality of new gripping surfaces that provide a universal gripping surface to accommodate various gripping configurations common in the medical field. The universal gripping surface provides a single catheter assembly which allows a user to grasp the catheter assembly in either a straight grip configuration, a ported grip configuration, or a winged grip configuration. Thus, the present invention may be used in any market in the world without requiring modification or special production to meet specialized gripping configurations common to that market. Additionally, the present catheter assembly includes various design features to ensure efficient insertion of the catheter.

The universal gripping surface of the current invention is designed to be used alone or in conjunction with current, traditional gripping surfaces and is designed to allow a "choked up" grip while preventing the "over the bevel" condition. The catheter assembly generally includes a needle hub and a catheter adapter, which are aligned along a common axis via an introducer needle. Each component is configured to interact and compatibly couple to provide an integrated apparatus. The needle hub and the catheter adapter further include various features to aid a user in gripping the catheter assembly, the combination of which forms a universal gripping surface.

Specifically, some embodiments of the catheter assembly include a universal gripping surface having a pair of oppositely positioned grips to accommodate opposing digits of a user. These oppositely positioned grips are generally located on the needle hub portion of the assembly and are pinched by the user to hold the catheter assembly in a straight grip configuration. The oppositely positioned grips may also include features, such as contours and textures, to further aid the user in securely gripping the surfaces.

Some embodiments of the catheter assembly further include a universal gripping surface having a paddle grip. The paddle grip is an outward extension of the needle hub that is positioned adjacent to the catheter adapter of the catheter assembly. The paddle grip is generally positioned to occupy a space adjacent to one side of the catheter adapter. As such, a user may pinch the paddle grip and control the catheter assembly from a winged grip configuration. The direct coupling between the paddle grip, the needle hub, and the introducer needle prevents an "over the bevel" condition from occurring during insertion of the catheter. In some embodiments, the paddle grip further includes a leading edge for accommodating a digit of the user to enable a port grip configuration.

Additionally, some embodiments include a securement platform forming a portion of the catheter adapter. The securement platform includes at least one wing-like extension generally positioned opposite the paddle grip. The securement platform may also include a leading edge for accommodating a digit of the user. The leading edge of the securement platform is used in conjunction with the leading edge of the paddle grip, and a thumb grip forming a proximal end of the needle hub, to enable a ported grip configuration. In some embodiments of the present invention, the thumb grip forms a base or proximal end of the needle hub and is a generally planar surface perpendicular to the oppositely positioned grips. In some implementations of the present invention, the thumb grip further includes a contour or a texture to increase friction between the needle hub and the thumb of the user.

The ported grip configuration is achieved via simultaneously contacting the leading edge of the securement platform with a first digit, contacting the leading edge of the paddle grip with a second digit, and contacting the thumb grip with a thumb. This three-point, ported grip configuration provides control and dexterity during insertion, as well as provides a bridging effect to prevent premature separation of the individual components of the catheter assembly, or an "over the bevel" condition.

Some embodiments of the present invention further include a guard feature. The guard feature is located on an outer surface of the needle hub of the catheter assembly, so as to be interposed between the oppositely positioned gripping surfaces and the catheter adapter. Specifically, the oppositely positioned gripping surfaces may include a guard feature whereby a portion of the gripping surfaces is extended outwardly thereby preventing a user's finger and thumb from inadvertently contacting a portion of the catheter assembly. The guard feature is provide as a physical barrier to permit a user to grasp the assembly in a straight grip configuration, yet prevent the user from inadvertently contacting the catheter adapter of the assembly. Inadvertent contact may result in premature separation of the components leading to an "over the bevel" condition. Thus, the guard feature prevents the occurrence of this condition.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1A:
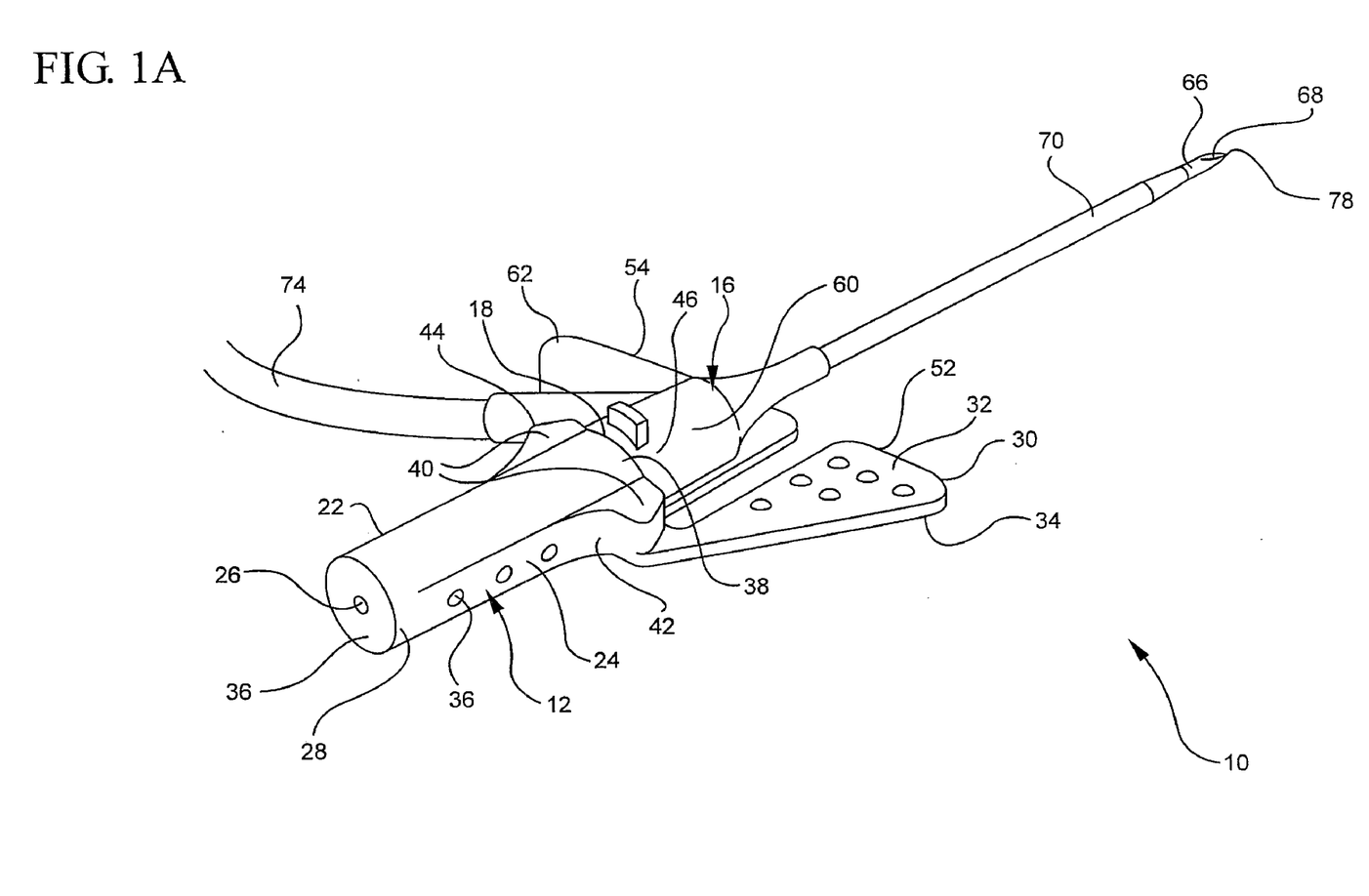
FIG. 1A is a perspective view of an embodiment of the present invention.

Referring now to FIG. 1A, a catheter assembly 10 is illustrated including a needle hub 12, and a catheter adapter 16. Each of the components 12 and 16 of the catheter assembly 10 is configured so as to cooperate as an integrated apparatus. Thus, each component 12 and 16 comprises features and elements to permit compatible engagement with the adjacent component.

For example, in one embodiment of the present invention the needle hub 12 comprises a docking hub 18 for receiving a proximal portion 46 of the catheter adapter 16. As such, the components 12 and 16 are aligned and coordinated via an introducer needle 66 which extends from the needle hub 12, through a needle port 14 of the catheter adapter 16 to provide an integrated apparatus 10, as more clearly seen in FIG. 1B below.

Figure 3:
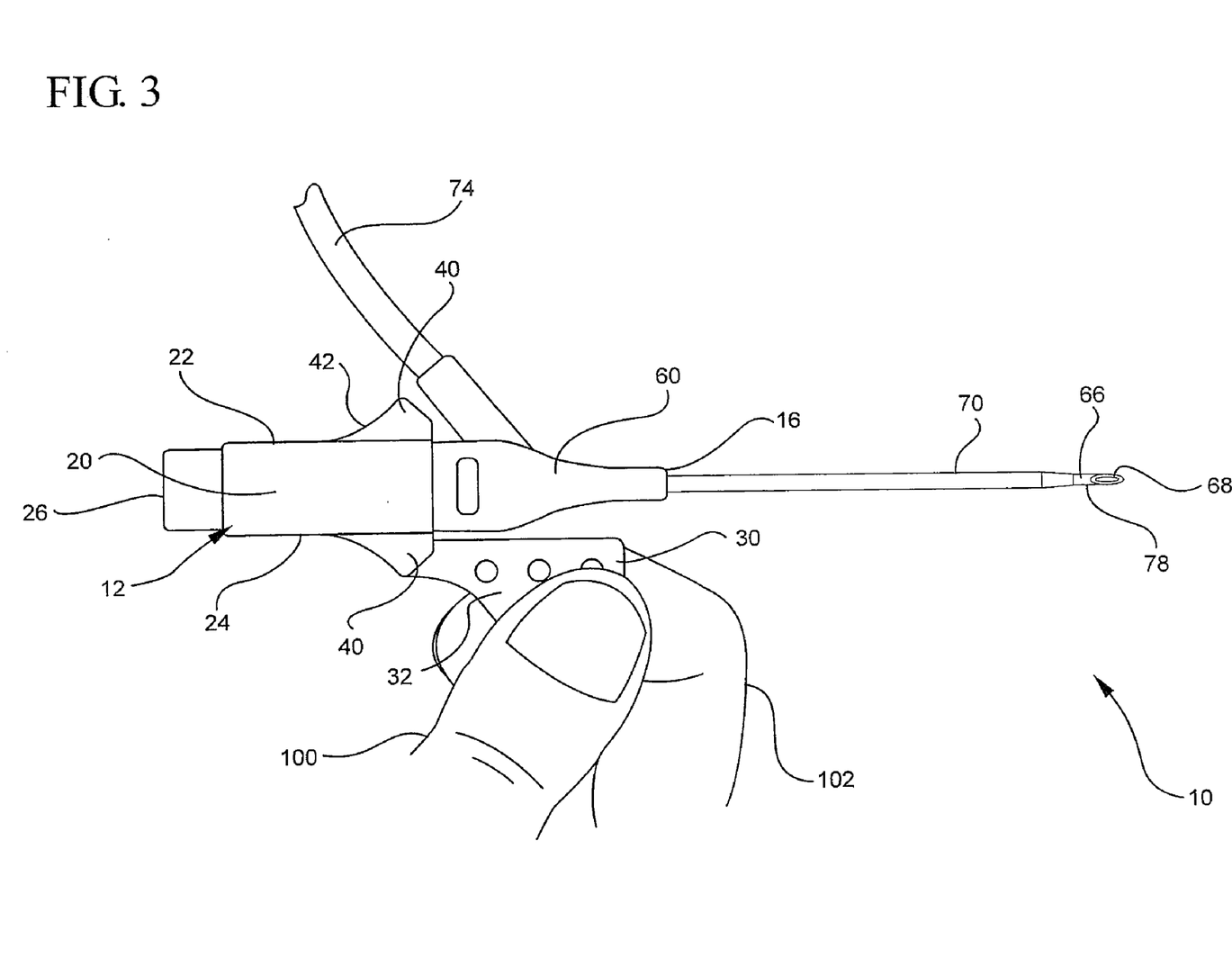
FIG. 3 is a perspective top view of an embodiment of the present invention held in a winged grip configuration.

The needle hub 12 further includes a plurality of surfaces and features to assist a user in grasping the catheter assembly 10 during insertion procedures. For example, in some embodiments of the present invention the needle hub 12 comprises a distal extension forming a paddle grip 30. The paddle grip 30 comprises a rigid or semi-flexible extension of the needle hub 12 having upper and lower gripping surfaces 32 and 34, respectfully. The paddle grip 30 is positioned adjacent to the body portion 60 of the catheter adapter 16 in a parallel orientation. In some embodiments, the paddle grip 30 occupies a space directly opposite a securement platform 62 of the catheter adapter 16. The upper 32 and lower 34 gripping surfaces of the paddle grip 30 are configured to accommodate opposing digits of a user, as shown in FIG. 3. As such, the paddle grip 30 enables a user to grasp the catheter assembly 10 in a winged grip configuration.

Figure 2:
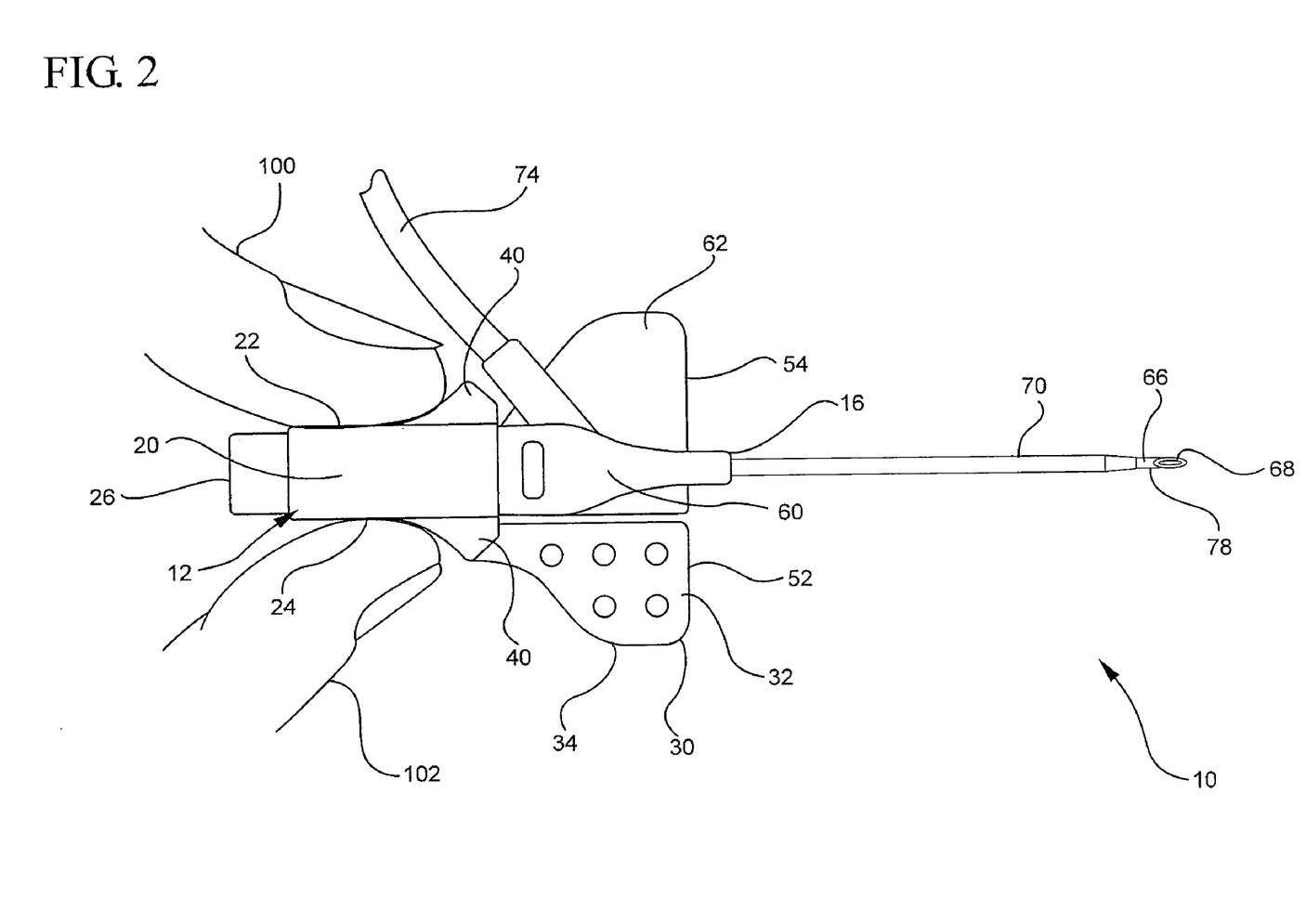
FIG. 2 is a perspective top view of an embodiment of the present invention held in a straight grip configuration.

In some implementations of the present invention, the needle hub 12 further includes a first gripping surface 22 and a second gripping surface 24. The first and second gripping surfaces 22 and 24 comprise parallel, opposing surfaces of the needle hub body 20. As configured, the gripping surfaces 22 and 24 permit a user to grasp the catheter assembly 10 in a straight grip configuration, as shown in FIG. 2. In some embodiments, the gripping surfaces 22 and 24 are contoured to further accommodate the physiological shape of the user's opposing digits. In other embodiments, the gripping surfaces 22 and 24 further include a texture or anti-slip coating 36 to increase friction between the user's digits and the needle hub 12. Still further, in some embodiments the gripping surfaces 22 and 24 comprise multiple contours to provide an ergonomic gripping surface.

The gripping surfaces 22 and 24 may further include a guard feature 40. The guard feature 40 generally comprises an outwardly extended portion of the gripping surface 22 and 24 which provides a physical barrier between the user's opposing digits and the catheter adapter 16 of the catheter assembly 10. In some embodiments, one or more gripping surfaces 22 and/or 24 comprise an outward, exponential curve 42, wherein the peak 44 of the curve 42 is the outermost surface of the guard feature 40. In other embodiments, the guard feature 40 comprises any physical barrier to prevent the user's grip from extending beyond the needle hub 12 to contact the catheter adapter 16. In some implementations of the present invention, a guard feature 40 is interposed between the body portion 20 of the needle hub 12, and the paddle grip 30.

Finally, in some implementations of the present invention the needle hub 12 further includes a thumb grip 26. The thumb grip 26 comprises the proximal end 28 of the needle hub 12 and provides a generally flat surface to accommodate a user's thumb. In some implementations of the present invention, the thumb grip 26 further includes a texture or anti-slip coating 36 to increase friction between the user's thumb and the needle hub 12. In some embodiments, the thumb grip 26 further includes a contoured surface to provide an ergonomic gripping surface.

Figure 4:
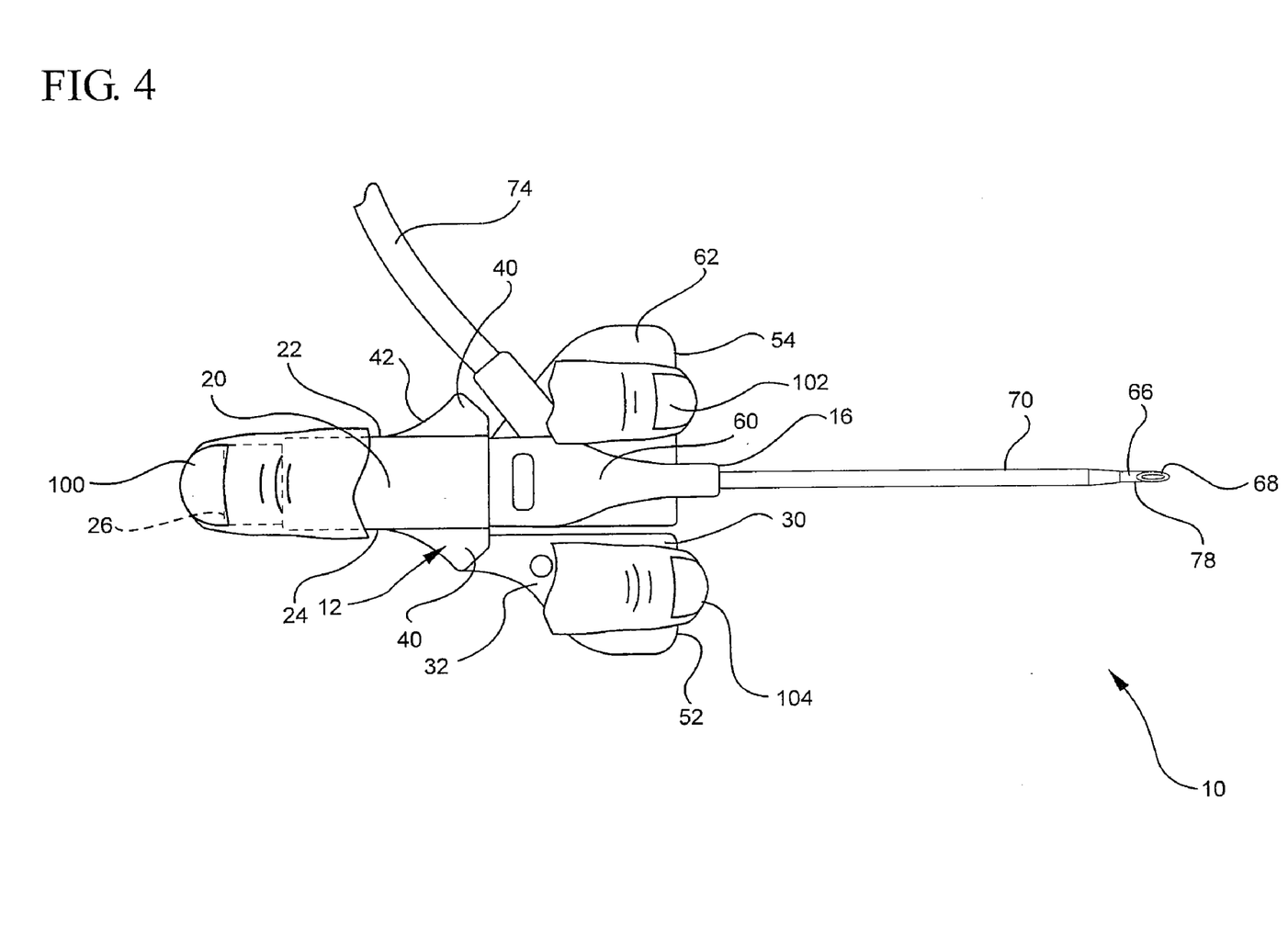
FIG. 4 is a perspective top view of an embodiment of the present invention held in a ported grip configuration.

The thumb grip 26 is generally used in conjunction with a leading edge 52 of the paddle grip 30, and a leading edge 54 of the securement platform 62 to enable a user to grasp the catheter assembly 10 in a ported grip configuration, as shown in FIG. 4. In some embodiments, the leading edge 52 of the paddle grip 30 is contacted with a first digit, such as an index finger, the leading edge 54 of the securement platform 62 is contacted with a second digit, such as a middle finger, and the thumb grip 26 is contacted with the thumb of the user in a ported grip configuration.

The multiple contact points 52, 54, and 26 of the ported grip configuration not only provides control, but also provides a bridging effect to prevent premature separation of the components 12 and 16 of the catheter assembly during insertion procedures. Premature separation of components 12 and 16 may lead to an "over the bevel" condition. The "over the bevel" condition occurs where the beveled portion 68 of the introducer needle 66 is withdrawn into the catheter 70 prior to the beveled portion 68 providing a sufficient opening in the patient for insertion of the catheter 70. This condition is often painful for the patient and may result in failed insertion, as well as various other undesirable complications. Thus, the various surfaces and features of the present invention provide a catheter assembly 10 having universal gripping surfaces which allow for multiple methods of gripping the catheter assembly 10, while preventing the "over the bevel" condition.

Figure 1B:
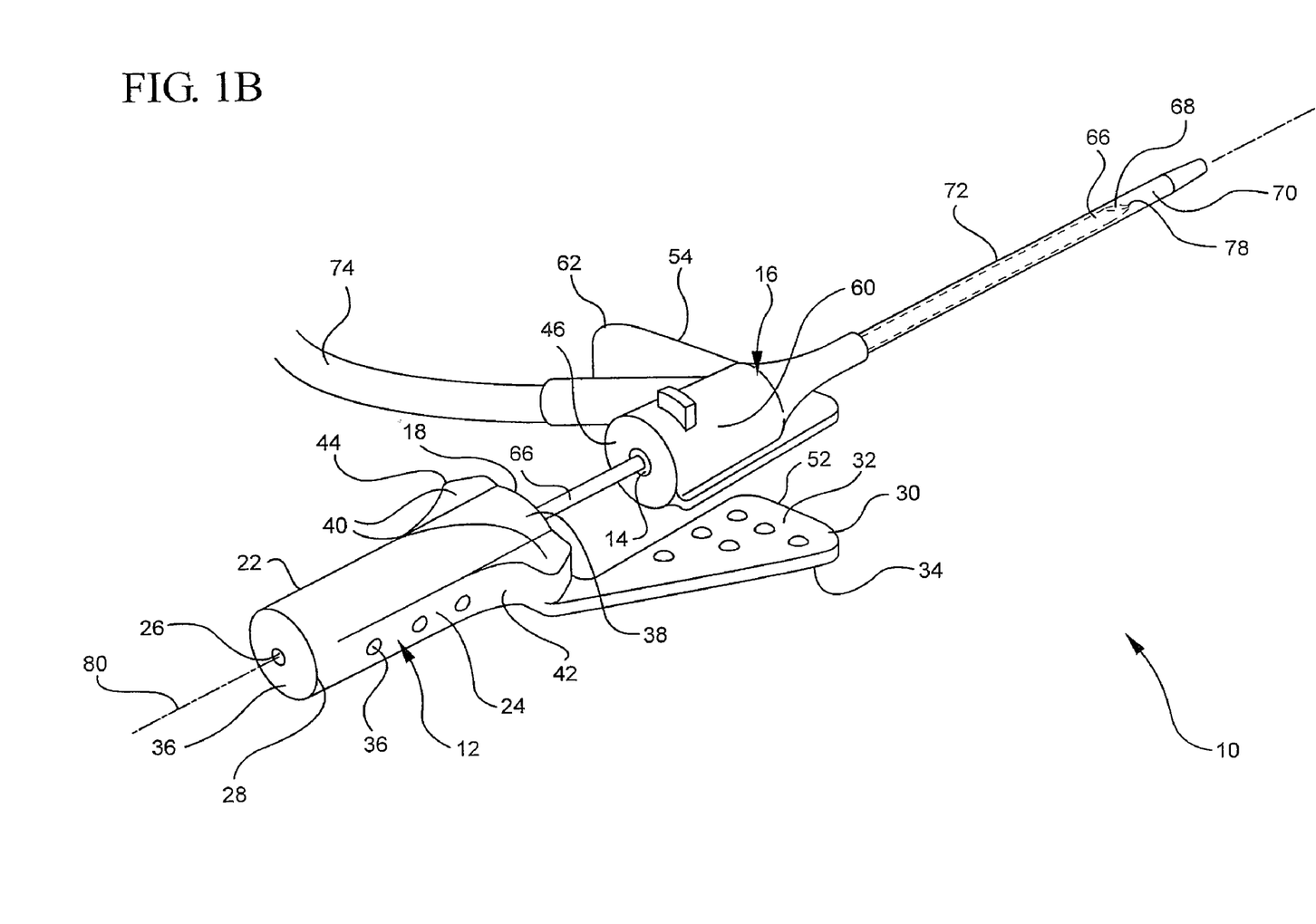
FIG. 1B is an exploded perspective view of FIG. 1.

Referring now to FIG. 1B, an exploded view of the catheter assembly 10 is shown. The components 12 and 16 are generally aligned along a longitudinal axis 80. The introducer needle 66 generally comprises a first end (not shown) fixedly attached to the needle hub 12, and a free end 72 extending outward therefrom. The free end 72 of the introducer needle comprises the beveled portion 68 and a needle tip 78 for providing an opening in the patient through which the catheter 70 is inserted. The catheter adapter 16 may also include a fluid line 74, or intravenous tubing for providing a fluid or medicament to the patient via the catheter 70. In some implementations of the present invention, the catheter adapter 16 further includes a clip or pawl (not shown) for retaining the distal end 38 of the needle hub 12. In these embodiments, the clip or pawl prevents separation of the needle hub 12 from the catheter adapter 16 until after the needle tip 78 has been withdrawn from the catheter adapter 16.

The needle hub 12 may further include design features to accommodate design features of the catheter adapter 16. For example, in some embodiments a portion of the distal end 38 of the needle hub body 20 is beveled to provide clearance for the fluid line 74 of the catheter adapter 16.

Referring now to FIG. 2, an implementation of the present invention is shown as held in a straight grip configuration. As shown, the first and second gripping surfaces 22 and 24 provide opposing surfaces to accommodate opposing digits 100 and 102 of a user. In some embodiments of the present invention, a thumb 100 of a user engages the first gripping surface 22 and an index finger 102 of a user engages the second gripping surface 24. In this manner, the user pinches the opposed gripping surfaces 22 and 24 of the needle hub 12 to grasp the catheter assembly 10. In some embodiments, the user grip is shifted distally towards the catheter adapter 16 into a "choked up" position. When held in a "choked up" position, the user's opposing digits 100 and 102 largely occupy or contact the guard feature 40 of the gripping surfaces 22 and 24. The "choked up" position may be desirable to provide increased control and leverage during insertion procedures. The presence of the guard features 40 permit the "choked up" position, yet prevent inadvertent contact between the user's digits 100 and 102, and the catheter adapter 16 of the catheter assembly 10.

Referring now to FIG. 3, an implementation of the present invention is shown as held in a winged grip configuration. As shown, the winged grip configuration is aided by the paddle grip 30. The paddle grip 30 is a rigid or semi-flexible extension of the distal end 38 of the needle hub 12. The paddle grip 30 includes a generally planar surface having a first side and a second side, wherein the first side comprises an upper surface 32 and the second side comprises a lower surface 34 (not clearly shown in FIG. 3, see FIGS. 1A and 1B). The paddle grip 30 is gripped by placing a first digit, such as a thumb 100, on the upper surface 32, and placing a second digit, such as an index finger 102, on the lower surface 34. The opposing digits 100 and 102 pinch the paddle grip 30 to secure the catheter assembly 10 in a winged grip configuration. Thus, some implementations of the catheter assembly 10 of the present invention comprise multiple surfaces and features to permit various methods of gripping the catheter assembly 10.

Referring now to FIG. 4, an implementation of the present invention is shown as held in a ported grip configuration. As shown, the ported grip configuration utilizes three-points of contact to grasp the catheter assembly 10. A thumb grip 26 provides a first point of contact, and is configured to receive a first digit of a user, for example a thumb 100. A leading edge 54 of the securement platform 62 provides a second point of contact, and is configured to receive a second digit of a user, for example an index finger 102. A leading edge 52 of the paddle grip 30 provides a third point of contact, and is configured to receive a third digit of a user, for example a middle finger 104. In this manner, the user contacts all three points 26, 52, and 54 to grasp the catheter assembly 10 in a ported grip configuration.

Figure 5:
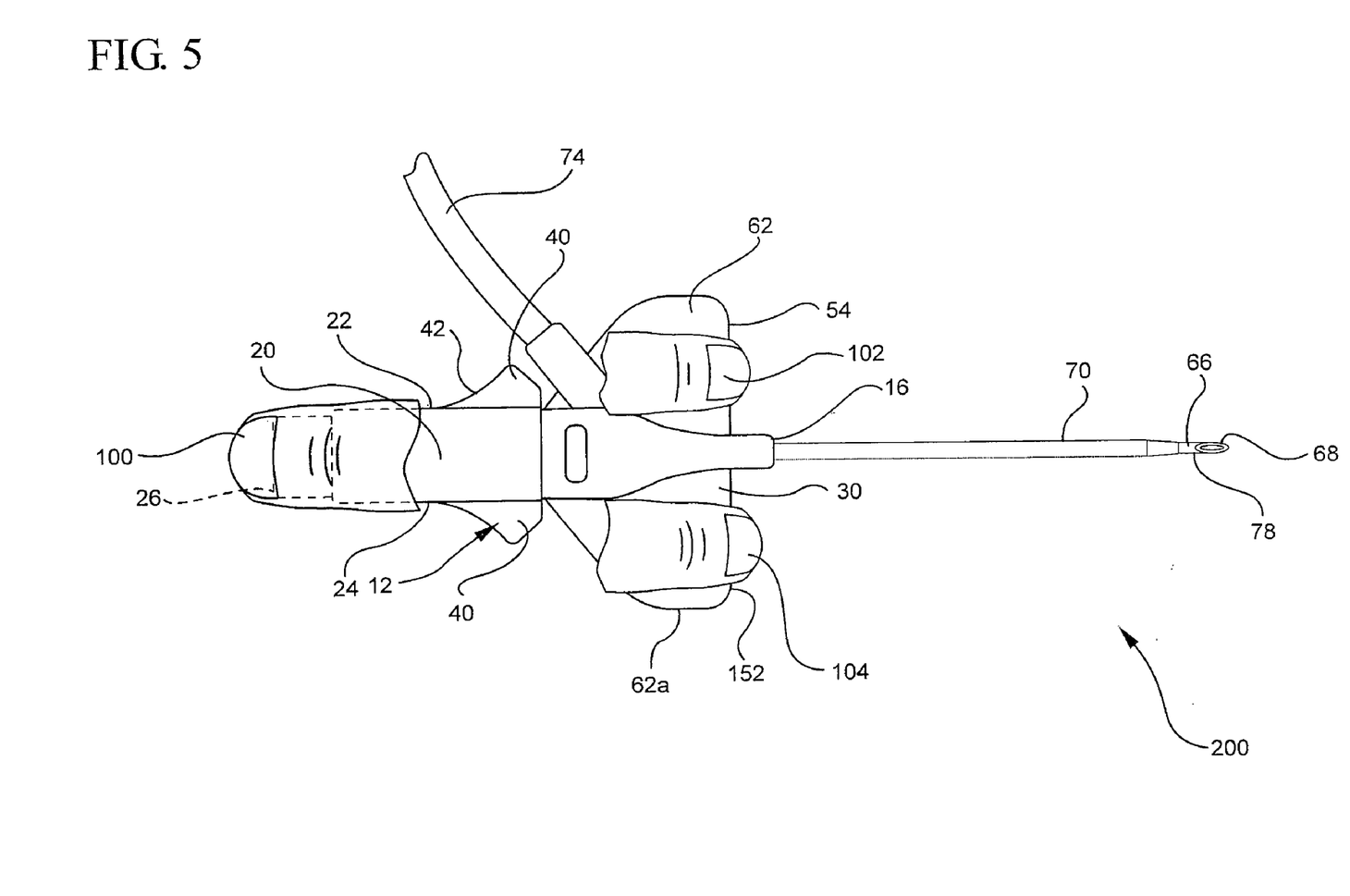
FIG. 5 is a perspective top view of an embodiment of the present invention held in a ported grip configuration.

Referring now to FIG. 5, an implementation of a catheter assembly 200 is shown. The catheter assembly 200 includes a second securement platform 62a positioned opposite the first securement platform 62 on the catheter adapter 16. The second securement platform 62a is positioned so as to have a leading edge 152 generally aligned with the leading edge 54 of the first securement platform 62. As such, the first securement platform 62, the second securement platform 62a and the thumb grip 26 provide surfaces by which the user may grasp the catheter assembly 200 in a ported grip configuration. Specifically, the thumb grip 26 provides a first point of contact, and is configured to receive a first digit of the user, for example a thumb 100. The leading edge 54 of the first securement platform 62 provides a second point of contact, and is configured to receive a second digit of the user, for example an index finger 102. The leading edge 152 of the second securement platform 62a provides a third point of contact, and is configured to receive a third digit of the user, for example a middle finger 104. In this manner, the user contacts all three points 26, 152, and 54 to grasp the catheter assembly 200 in a ported grip configuration.

Figure 6:
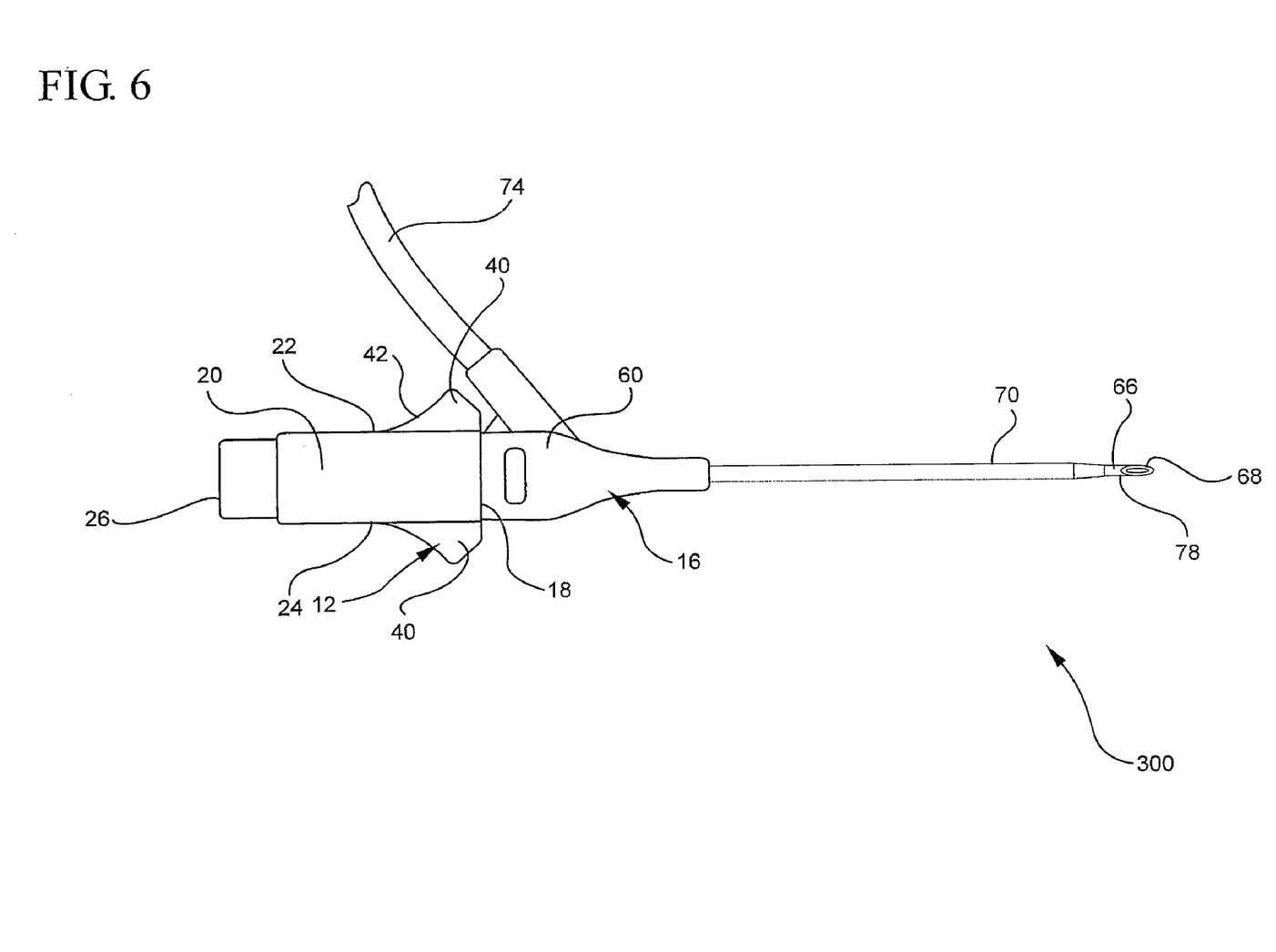
FIG. 6 is a perspective top view of an embodiment of the present invention having guard features and limited gripping surfaces.

Referring now to FIG. 6, an implementation of a catheter assembly 300 is shown. Some embodiments of the present invention may be modified to limit the methods of gripping the catheter assembly. For example, catheter assembly 300 has been modified to accommodate only a straight grip configuration. Specifically, the catheter adapter 160 has been modified to exclude securement platforms 62 and 62a of catheter adapter 16, and paddle grip 30 of needle hub 12, as shown in FIGS. 1-5, above. By removing these features 62, 62a and 30, the catheter assembly 300 eliminates the possibility of either a ported or winged grip configuration. Modifications such as these may be desirable for markets or industries where a specific grip configuration is desirable, or more common than others. Modifications such as these may also reduce manufacturing costs, as well as eliminate unnecessary features for a given market. In some embodiments, catheter assembly 300 further includes guard features 40 to prevent an "over the bevel" condition during insertion.

Figure 7:
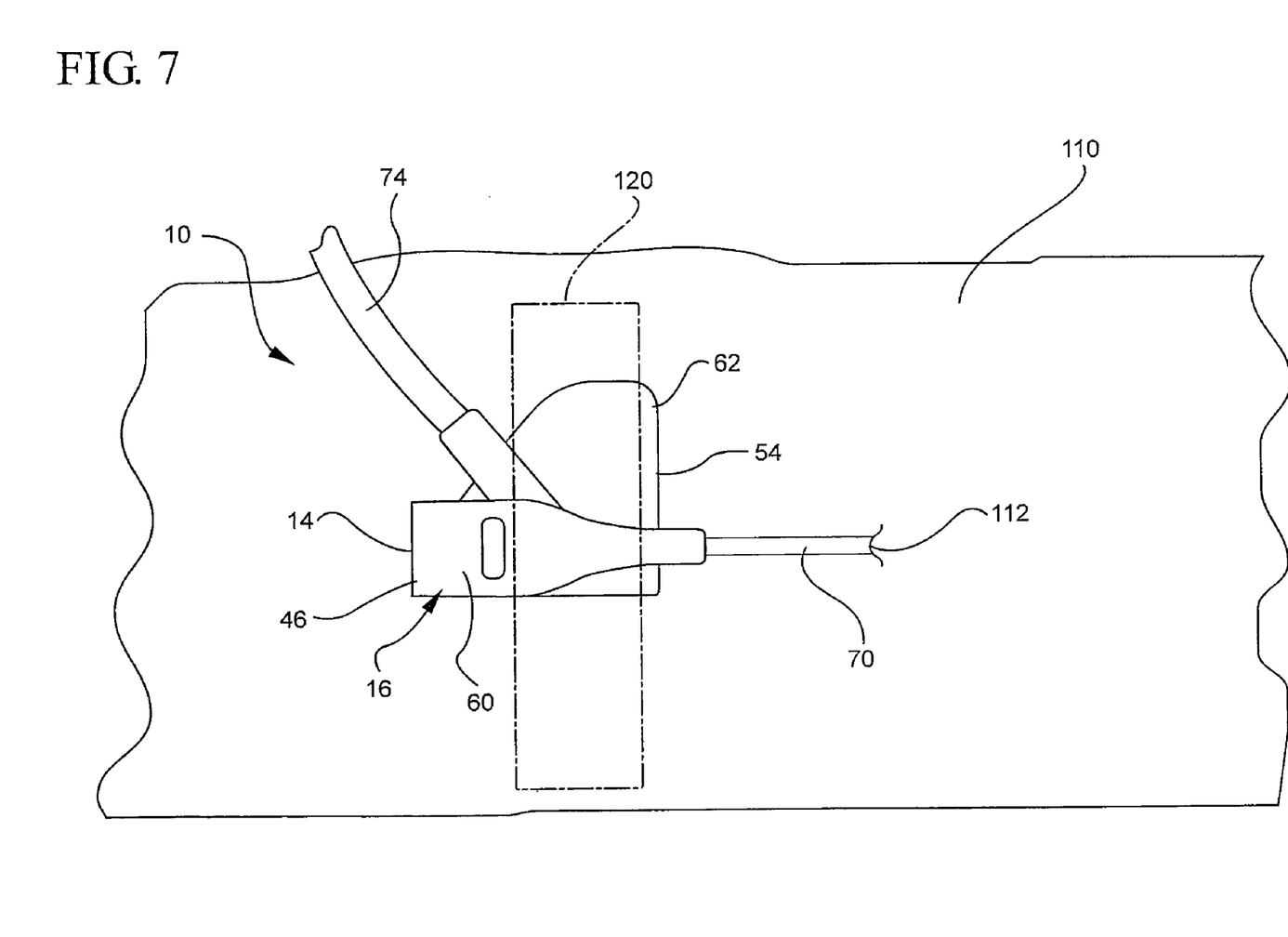
FIG. 7 is a perspective view of an embodiment of the present invention following insertion into a patient.

Referring now to FIG. 7, a catheter adapter 16 shown following insertion of the catheter 70 into a patient 110 and removal of the introducer needle 66 from the adapter 16. Following insertion of the catheter 70, the securement platform 62 provides a planar surface by which to secure the catheter adapter 16 to the patient 110 via an adhesive strip 120. As such, the catheter adapter 16 is prevented from rotating relative to the patient 110 and maintains the position of the catheter 70 within the insertion site 112 of the patient.

The present invention provides a conventional integrated catheter assembly having universal gripping surfaces. The present invention further permits a user to grasp the catheter assembly in a variety of gripping positions without the possibility of creating an "over the bevel" condition. Accordingly, the present invention is adapted to provide a useful, safe, and universal gripping surface for balanced, controlled handling of catheter assemblies during insertion of a catheter.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An intravenous catheter device, comprising:
    a catheter adapter having a proximal portion located opposite a catheter;
    a needle hub having a distal end and a proximal end, the distal end being removably coupled to the proximal portion of the catheter adapter, the needle hub including a fixedly attached needle extending outwardly therefrom;
    a first gripping surface disposed on a first side of the needle hub;
    a second gripping surface disposed on a second side of the needle hub opposite the first side;
    a first guard feature protruding outwardly from a distal end of first gripping surface, the first guard feature being shaped and sized to providing a physical barrier between a first digit on the first gripping surface and the catheter adapter;
    a second guard feature protruding outwardly from a distal end of second gripping surface, the second guard feature being shaped and sized to providing a physical barrier between a second digit on the second gripping surface and the catheter adapter;
    a securement platform extending laterally outward from a first side of the catheter adapter to provide a leading edge, the securement platform having a planar surface in a first plane, wherein the first plane is generally perpendicular to the gripping surface of the needle hub; and
    a paddle grip extending outwardly from a portion of the distal end of the needle hub, the paddle grip being positioned adjacent to the catheter adapter and opposite the securement platform, the paddle grip having a leading edge and further having a planar surface in a second plane that is generally parallel to the first plane.

2. The catheter device of claim 1, wherein the leading edge of the securement platform and the leading edge of the paddle grip are oppositely positioned and approximately parallel, the leading edge of the securement platform being capable of accommodating a first digit, the leading edge of the paddle grip being is capable of accommodating a second digit, and the proximal end of the needle hub being capable of accommodating a thumb to enable a ported grip of the catheter device, and wherein a portion of the securement platform is configured to accommodate opposing digits to enable a winged grip of the catheter device.

3. The catheter device of claim 2, wherein the first guard feature is interposed between the first gripping surface and the securement platform.

4. The catheter device of claim 3, wherein each of the first gripping surface and the second gripping surface comprises a contoured feature capable of accommodating ergonomic features of the opposing digits.

5. The catheter device of claim 1, wherein the paddle grip comprises a top surface and a bottom surface, the top surface capable of accommodating a thumb, and the bottom surface capable of accommodating an opposing digit whereby the paddle grip is pinched between the thumb and the opposing digit to enable a winged grip of the catheter device.

6. The catheter device of claim 5, wherein the second guard feature is interposed between the second gripping surface and the paddle grip.

7. The catheter device of claim 5, further comprising a first leading edge forming a distal portion of the paddle grip, wherein the first leading edge is configured to accommodate a second digit.

8. The catheter device of claim 7, further comprising a securement platform fixedly attached to the catheter adapter, and positioned generally opposite the paddle grip, wherein the securement platform comprises a second leading edge approximately parallel to the first leading edge of the paddle grip and configured to accommodate a first digit, wherein the second leading edge, the first leading edge, and the proximal end are contacted with the first digit, the second digit, and the thumb, respectively, to enable a ported grip of the catheter device.

9. The catheter device of claim 1, wherein a portion of the guard feature comprises a portion of the gripping surface.

10. The catheter device of claim 1, wherein the proximal portion of each of the first guard feature and the second guard feature each curve outwardly from the first gripping surface and the second gripping surface, respectively.

11. The catheter device of claim 1, wherein a distal edge of the securement platform comprises a first leading edge to support a first digit, and a distal edge of the paddle grip comprises a second leading edge to support a second digit, wherein the first leading edge, the second leading edge and the proximal end of the needle hub are contacted with the first digit, the second digit and the thumb, respectively, to enable a ported grip of the catheter device.

12. An intravenous catheter device, comprising:
    a catheter adapter having a proximal portion located opposite a catheter;
    a needle hub having a distal end and a proximal end, the distal end being removably coupled to the proximal portion of the catheter adapter; and
    a paddle grip extending distally from the distal end of the needle hub and positioned adjacent to the catheter adapter, the paddle grip being shaped and sized to accommodate a first digit on a top surface of the paddle grip and a second digit on a bottom surface of the paddle grip, wherein the paddle grip is positioned opposite a securement platform of the catheter adapter, a first gripping surface disposed on a first side of the needle hub;

a second gripping surface disposed on a second side of the needle hub opposite the first side;

a first guard feature protruding outwardly from a distal end of the first gripping surface, the first guard feature being shaped and sized to providing a physical barrier between a user's digit on the first gripping surface and the catheter adapter; and a second guard feature protruding outwardly from a distal end of the second gripping surface, the second guard feature being shaped and sized to providing a physical barrier between a user's digit on the second gripping surface and the catheter adapter.

* * * * *